(12) United States Patent
Fazekas et al.

(10) Patent No.: US 11,346,712 B2
(45) Date of Patent: May 31, 2022

(54) SUN SAFETY DEVICE

(71) Applicant: VANESSA RESEARCH, INC., Hamden, CT (US)

(72) Inventors: Ferenc Fazekas, Hamden, CT (US); Norman Gray, Hamden, CT (US)

(73) Assignee: Vanessa Research, Inc., Hamden, CT (US)

(*) Notice: Subject to any disclaimer, the term of this patent is extended or adjusted under 35 U.S.C. 154(b) by 0 days.

(21) Appl. No.: 17/042,112

(22) PCT Filed: Aug. 9, 2018

(86) PCT No.: PCT/US2018/045894
§ 371 (c)(1),
(2) Date: Sep. 26, 2020

(87) PCT Pub. No.: WO2019/190586
PCT Pub. Date: Oct. 3, 2019

(65) Prior Publication Data
US 2021/0018361 A1 Jan. 21, 2021

Related U.S. Application Data

(60) Provisional application No. 62/647,893, filed on Mar. 26, 2018.

(51) Int. Cl.
*G01J 1/42* (2006.01)
*A61B 5/00* (2006.01)
*G01J 1/02* (2006.01)

(52) U.S. Cl.
CPC .............. *G01J 1/429* (2013.01); *A61B 5/441* (2013.01); *G01J 1/0219* (2013.01); *G01J 2001/4266* (2013.01)

(58) Field of Classification Search
CPC .. G01J 1/429; G01J 1/0219; G01J 2001/4266; A61B 5/441
See application file for complete search history.

(56) References Cited

U.S. PATENT DOCUMENTS 4,975,584 A 12/1990 Benjamin
5,107,123 A 4/1992 Shi
(Continued)

FOREIGN PATENT DOCUMENTS

ES 1071695 U 3/2010
NZ 548411 A 7/2008

OTHER PUBLICATIONS

Anonymous, "Innovative Sun Safety Solution tested in Wallingford and Milford, CT", Solaware, https://solawareindex.com/2017/08/29/innovative-sun-safety-solution-tested-in-wallingford-and-milford-ct/, Aug. 29, 2017, pp. 1-5.
(Continued)

*Primary Examiner* — Kiho Kim
(74) *Attorney, Agent, or Firm* — Dilworth IP, LLC

(57) ABSTRACT

The sun safety display and dispenser is a rugged outdoor device designed to measure the direct and scattered UV radiation in the atmosphere; to calculate and display a sun safety awareness index warning of the time to skin burn and or potential damage; to provide a personalized sun safety awareness index reading to help the user determine the appropriate SPF sunscreen, manually or automatically; and, to dispense sunscreen generally or by specific SPF as correlated with the user's personalized sun safety awareness index reading.

22 Claims, 8 Drawing Sheets

(56) References Cited

U.S. PATENT DOCUMENTS

| | | |
|---|---|---|
| 7,057,183 B2 | 6/2006 | May |
| 8,793,212 B2 | 7/2014 | McGuire |
| 2016/0100764 A1 | 4/2016 | Teich |
| 2016/0209265 A1 | 7/2016 | Lapiere |
| 2018/0224822 A1* | 8/2018 | Potucek ............... G05B 19/054 |
| 2018/0322255 A1* | 11/2018 | Connell, II ............ G16H 40/67 |
| 2019/0060678 A1* | 2/2019 | Poutiatine ............ A61B 5/1032 |

OTHER PUBLICATIONS

Extended European Search Report for App. No. EP18912895.2, dated Oct. 18, 2021, 8 pages.

* cited by examiner

SUN SAFETY DEVICE

FIELD OF THE INVENTION

The present invention relates to a Sun Safety Display and Dispenser device that is the combination of a local, real-time ultraviolet (UV) radiation warning system, a simplified sun safety educational guide, and in further embodiments a personalized monitoring device and a sunscreen dispenser.

BACKGROUND OF THE INVENTION

It is well known that excessive exposure to sunlight can be harmful and lead to an increased risk for skin cancer and other types of skin damage, such as wrinkles and loss of elasticity. However, many people spend a significant amount of their time outdoors under direct and reflected sun exposure; and are often unaware of their exposure and the required level of UV protection that would be required at a specific time and location.

The United States Environmental Protection Agency (EPA) has developed a UV Index (UVI) scale that conforms with international guidelines for UV reporting established by the World Health Organization. This scale is an 11 point plus scale divided into five color-coded categories that correspond to UV index for sun exposure. These levels are:

A UV Index reading of 0 to 2, or green, means low danger from the sun's UV rays for the average person.

A UV Index reading of 3 to 5, or yellow, means moderate risk of harm from unprotected sun exposure.

A UV Index reading of 6 to 7, or orange, means high risk of harm from unprotected sun exposure. Protection against skin and eye damage is needed.

A UV Index reading of 8 to 10, or red, means very high risk of harm from unprotected sun exposure. This level requires taking extra precautions because unprotected skin and eyes will be damaged and can burn quickly.

A UV Index reading of 11 or more, or purple, means extreme risk of harm from unprotected sun exposure. This level requires taking all precautions because unprotected skin and eyes can burn in minutes.

However, current public UV Index measuring units only focus on the direct atmospheric sunlight, and display the results in a globally accepted, but not well known or understood measure, called the UV Index (UVI) scale. The UVI scale is not easily and immediately interpretable for the fast-moving outdoor audience (passengers walking in crowded cities, runners in parks, families heading to the beach/pool, etc.).

At a time of rising incidence of skin cancer, this information is useful for raising public awareness about the invisible dangers of sun overexposure at the location of the exposure; and further, providing the education and preventive safety solution, namely the appropriate sunscreen.

The available real-time information sources about sun safety are limited in the sense that they require proactive approach from the individuals; that is, they have to listen to and or read the weather forecast, download a smartphone application, or buy and use a wearable device with either limited accuracy or limited availability. Additionally, forecast-based technologies, which are often based on a single measurement point for a whole region, or as a forecast based on mathematical models, such as a weather report or smartphone app are not necessarily accurate or appropriate for the given local conditions, where the actual local UV index can vary with 1 or even 2 units on the UV Index scale. Therefore, a one-point difference can mean a higher UV risk for the individual. Also, these forecast models and personal UV sensors do not take into account or measure the reflection of UV light from different surfaces such as water, sand, concreate, snow, etc. at a specific location. The effect of reflected UV radiation can be significant and add to the effects of the direct atmospheric UV radiation.

In addition to these limitations, the current systems do not take in to account the skin type or susceptibility to UV radiation exposure damage of a user. Human skin tones and skin types various greatly in terms of color and pigmentation due to melanin content and dispersion. Thus, the susceptibility and tolerance to sun exposure can vary greatly from individual to individual. The 11+ point UVI scale described above is generalized for the average individual and does not take in to account the specific sun tolerance of the individual. For example, the Fitzpatrick scale provides a numerical classification for human skin color to estimate the response of different types of skin to UV light. The scale was initially developed on the basis of skin and eye color, but has been modified to be based on the patient's reports of how their skin responds to the sun; and remains a recognized tool for dermatological research into human skin pigmentation. The Fitzpatrick scale is divided into the following 6 skin types:

Type I (scores 0-6) always burns, never tans.
Type II (scores 7-13) usually burns, tans minimally.
Type III (scores 14-20) sometimes mild burn, tans uniformly.
Type IV (scores 21-27) burns minimally, always tans well.
Type V (scores 28-34) very rarely burns, tans very easily.
Type VI (scores 35-36) never burns.

The device, systems, and methods of the present invention seek to solve the problems inherent with current UV monitoring and reporting technologies. The device, systems, and methods of the present invention also seek to solve the further problem of providing an UV exposure risk assessment based on the skin characteristics of the individual.

It is apparent from the foregoing there is an ongoing need for developing a locally deployable, real-time sun safety warning solution device for any given public/outdoor place where people would spend time, even if it is only 10-15 min. There is a need for such a system that is accurate, easy to understand and use, and which in certain embodiments provides a personalized UV index tailored to the particular user's skin type. Furthermore, there is a need for such a system that can also deliver the appropriate level and amount of sunscreen for the user at that location under the current conditions.

SUMMARY OF THE INVENTION

We surprisingly found that if we display a certain easy-to-interpret number about the possible risk of skin damage (including, but not limited to sunburns, early skin aging, skin cancer (all 3 types), and eye damage) to the public, individuals are more likely to engage in sun protective behaviors to prevent skin and eye damage.

The present invention relates to a Sun Safety Display and Dispenser device that is the combination of a local, real-time ultraviolet (UV) radiation warning system, a simplified sun safety educational guide, and in further embodiments a personalized monitoring device and a sunscreen dispenser.

DETAILED DESCRIPTION OF THE INVENTION

Figure 1:
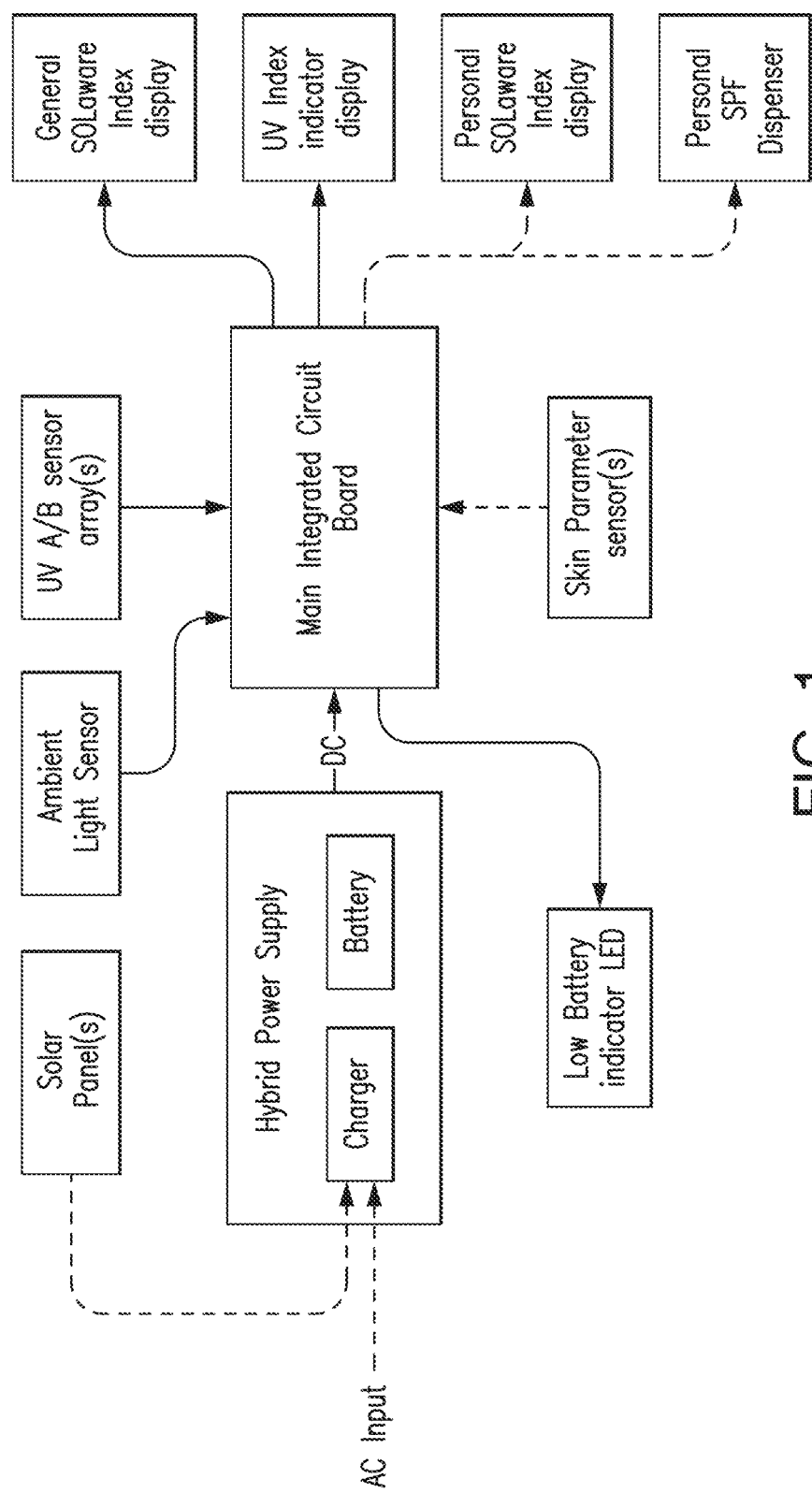
FIG. 1 shows a block diagram of the components of an embodiment of the device of the present invention.

The present invention relates to:

1. A device for monitoring and displaying solar exposure risk for human skin comprising:
   (a) two or more light sensing detectors for measuring the instantaneous solar energy density [in $(mW/cm^2)$] at a location in proximity to a human subject,
   (b) a computer system for calculation of the solar exposure risk, the computer system comprising,
      (i) a computer processor,
      (ii) a computer readable storage device, and
      (iii) a computer program,
   (c) one or more display monitors,
   (d) one or more interfaces connecting the light sensing detectors to the computer system,
   (e) one or more optional interfaces connecting the two or more light sensing detectors, and
   (f) an interface connecting the computer system to the display monitor,
   wherein the device displays an instantaneous solar exposure risk for human skin based on the instantaneous solar energy density.

2. A device according to claim 1 wherein at least one of the light sensing detectors is oriented to detect and measure the direct solar energy density and wherein at least one of the light sensing detectors is oriented to detect and measure reflected solar energy density.

3. A device according to claim 1 further comprising a means for continuously moving the light sensing detectors.

4. A device according to claim 3 wherein the means for continuously moving the light sensing detectors moves the detectors in an oscillating motion through a partial circular path of up to about 300 degrees, and even a full circular path.

5. A device according to claim 1 that further comprises a component for measuring one or more skin characteristics of a human subject, and wherein the device calculates and displays an output parameter that further comprises an individualized solar exposure risk level for the human subject.

6. A device according to claim 5 wherein the one or more skin characteristics are selected from skin color, melanin content, melanin density, skin temperature, and moisture content.

7. A device according to claim 5 wherein the output parameter further comprises a sunscreen application recommendation for the human subject.

8. A device according to claim 7 that further comprises a module for containing and dispensing a sunscreen product.

9. A device according to claim 8 that dispenses the appropriate sunscreen product based on the output parameter for the human subject.

10. A device according to claim 1 wherein the two or more light sensing detectors are movable.

11. A device according to claim 10 wherein the two or more light sensing detectors are movable using an automated device for tracking the solar energy.

12. A device according to claim 1 wherein the display monitor displays an instantaneous solar exposure risk in digital format as a numerical value.

13. A device according to claim 1 wherein the display monitor displays an instantaneous solar exposure risk in digital format as a color coded value.

14. A device according to claim 1 further comprising a mounting pole.

15. A device according to claim 2 further comprising a base into which the mounting pole is mounted.

16. A device according to claim 15 that is stationary.

17. A device according to claim 15 that is mobile.

18. A device according to claim 1 wherein the device displays an instantaneous generalized solar exposure risk for human skin based on the instantaneous solar energy density.

19. A device according to claim 1 wherein the device displays an instantaneous personalized solar exposure risk for human skin based on the instantaneous solar energy density.

20. A method for providing a general solar exposure risk index for human skin using the device of claim 1.

21. A method for providing a personalized solar exposure risk index for human skin using the device of claim 1.

22. A method for providing a personalized solar exposure risk index for human skin and dispensing an appropriate amount and SPF level of a sunscreen product using the device of claim 1.

These and other aspects of the present invention will become apparent from the disclosure herein.

Sun Safety Display and Dispenser Device

In an embodiment, the solar sun safety display and dispenser device of the present invention is designed to provide
   (i) easily understandable sun safety warnings in the form of a sun safety awareness index, such as a solar intensity index, based on a real-time, local UV radiation measurement from the combination of direct sunlight and the reflected UV rays from the surrounding surfaces, obtained from two or more sensors with stationary or rotational arrangement;
   (ii) a reading of the personalized sun safety awareness index to determine the optimum sun protection factor (SPF) sunscreen;
   (iii) education about the dangers represented by the sun safety awareness index and general information about sun overexposure; and,
   (iv) the dispensing of the appropriate SPF sunscreen In an embodiment, the solar safety and display dispenser device of the present invention is a combination of
   (i) a custom-made UV sensor (unique array, movement, and field of view);
   (ii) a custom circuitry that uses an algorithm to calculate the sun safety awareness index;

(iii) an electronic real-time display that shows the sun safety awareness index;
(iv) a sun safety educational board-static or electronic;
(v) a skin scanner to determine the personalized sun safety awareness index;
(vi) a rechargeable battery with or without a solar panel power source;
(vii) a sunscreen dispenser singly or integrated with the personalized monitoring sensor; and
(viii) a metal base structure designed to withstand hurricane winds of up to 150 mph and heat temperatures ranging from −25 C to 150 C.

FIG. 1 shows a block diagram of the components of an embodiment of the device of the present invention. It is seen that the device comprises an AC input, one or more solar panels for providing energy for running the device, and a hybrid power supply comprising a charger and battery. The power supply provides direct current to the main integrated circuit board and other components. Inputs to the main integrated circuit board include an ambient light sensor, one or more, but preferably two or more UV (UVA/UVB) detectors for detecting direct and reflected light, and a sensor for measuring various skin parameters such as skin color or tone, skin moisture, skin temperature, etc. Outputs from the main integrated circuit board include a general sun safety awareness index display, a UV index indicator display, a personal sun safety awareness index display, a personal sunscreen dispenser for dispensing a sunscreen product of appropriate SPF level, and a low battery LED indicator.

Figure 2:
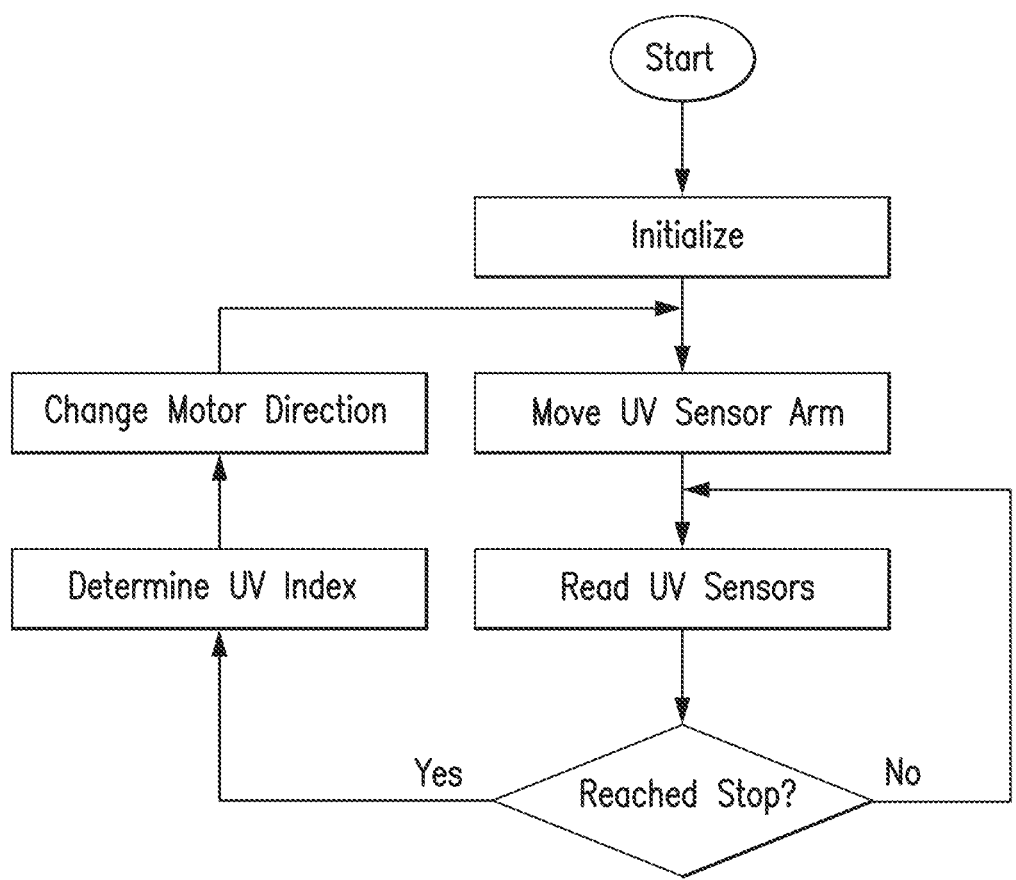
FIG. 2 shows a flow chart of the operation of the UV sensors of an embodiment of the device of the present invention.

FIG. 2 shows a flow chart of the operation of the UV sensors of an embodiment of the device of the present invention. The UV sensors can be moved in various directions to detect both direct and reflected UV radiation.

Figure 3:
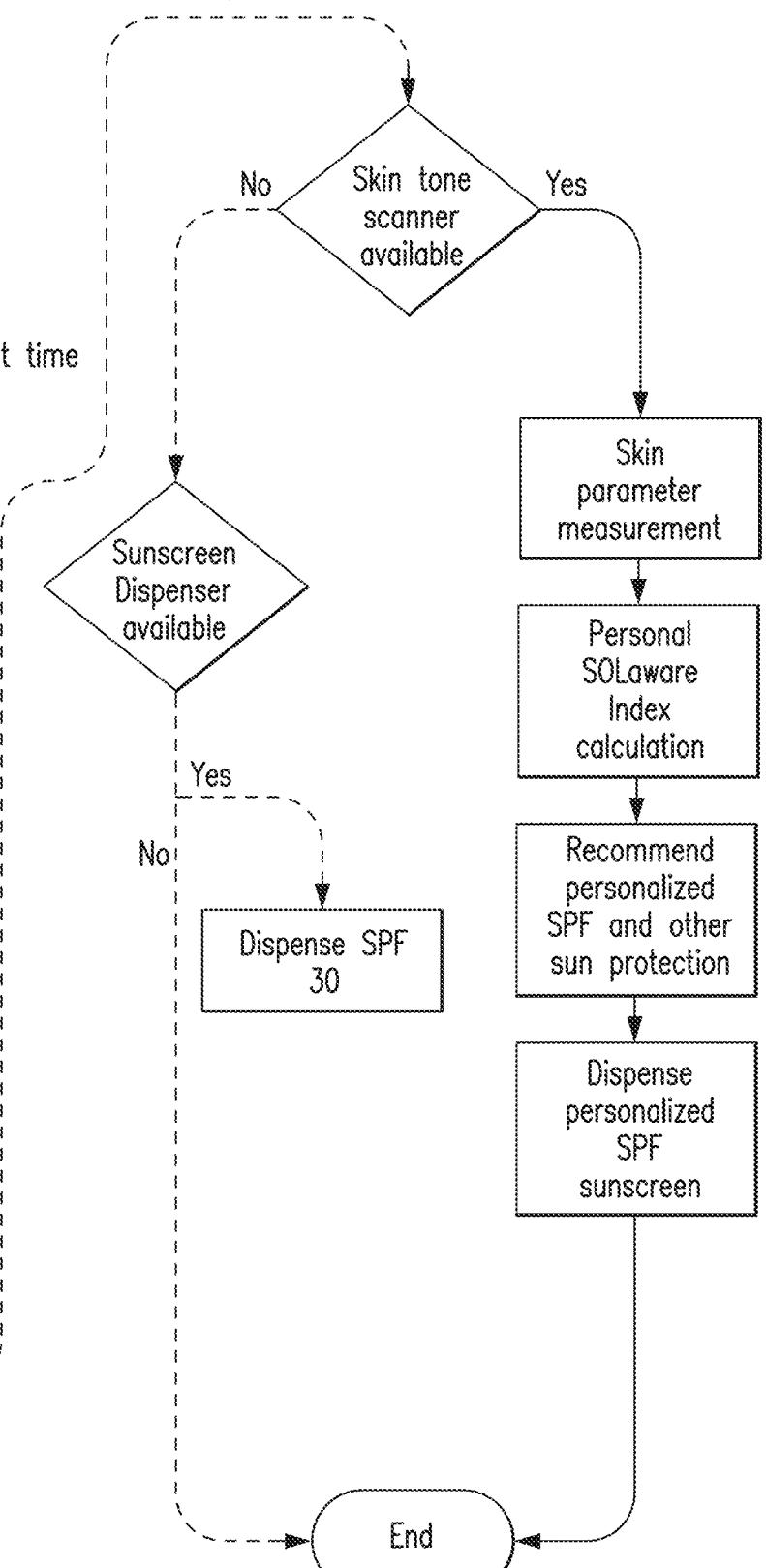
FIG. 3 shows a flow chart for the overall operation of the device of the present invention.

FIG. 3 shows a flow chart for the overall operation of the device of the present invention. The core functionality for the device is shown on the left hand side of the chart. Optional functionality, as per alternative embodiments of the present invention are shown on the right hand side of the chart. These alternative embodiments can include skin tone scanner and a sunscreen dispenser.

Figure 4:
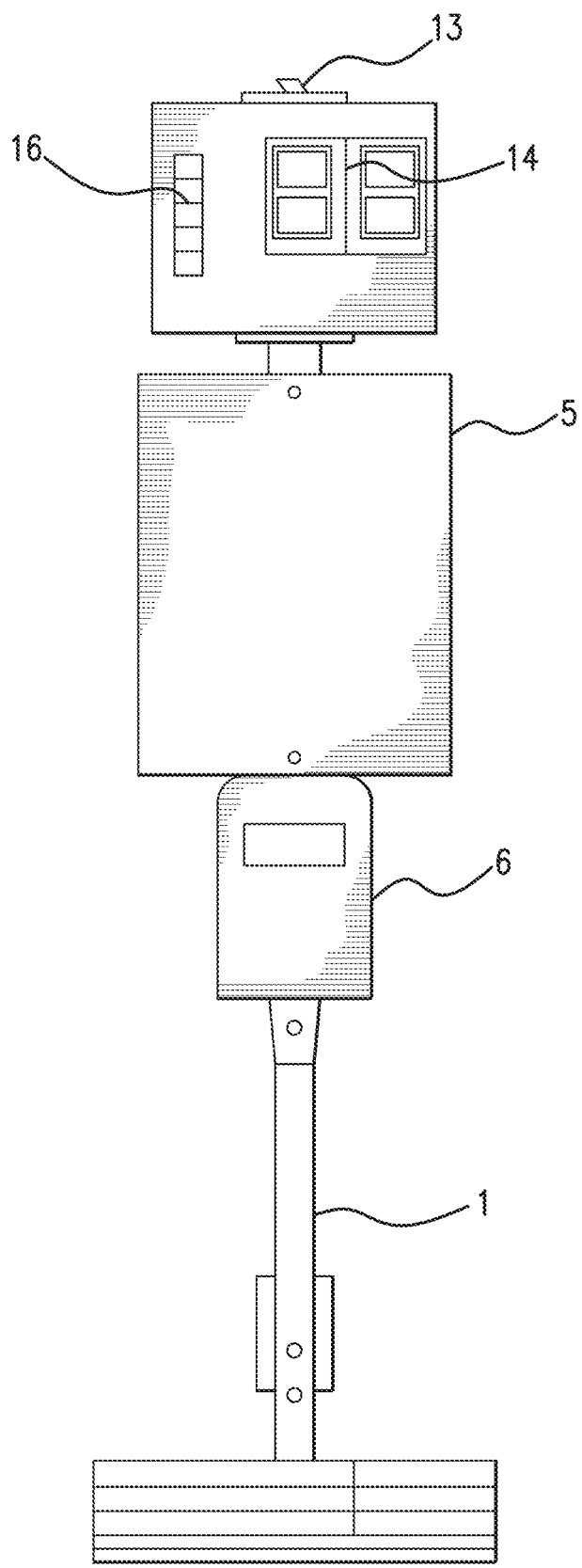
FIG. 4 is a front view of an embodiment of the device of the present invention illustrating the components of the device.

FIG. 4 is a front view of an embodiment of the device of the present invention illustrating the components of the device. Shown are a pole, 1, such as a galvanized steel pole, used to mount display pieces; an informational board, 5, used to relay solar safety information; a dispenser, 6, to dispense a sunscreen product of appropriate SPF value; the front view of the head unit with full assembly flip digits, 14, used to show the general sun safety awareness index; colored LEDs or other digital or electromechanical structure, 16, used to show UV index on scale, with optionally increased flashing of lights based on the intensity of the UV radiation; and UV sensor cluster 13 comprising one or multiple UVA/UVB sensor(s) and its rotational engine comprised of a rotational motor, a motor controller board, a magnetic arm and UV sensor holder arm, used to enable a controlled rotation of the UV sensor(s).

Figure 5:
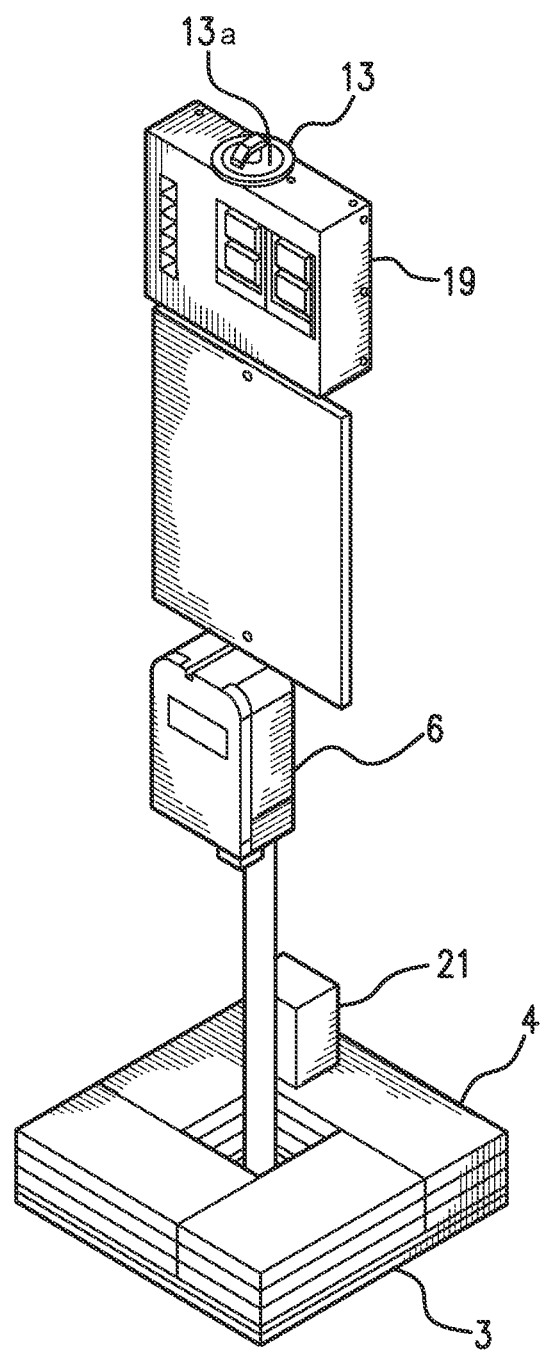
FIG. 5 is a perspective view of an embodiment of the device of the present invention illustrating the components of the device.

FIG. 5 is a perspective view of an embodiment of the device of the present invention illustrating the components of the device. Shown are: a base, 3, such as a wooden or metal base, to bolt onto and secure the pole, 1; concrete bricks, 4, or other weights constructed to add weight and stability for security for safety reasons; a head unit box, 19, built to house the components and electronic hardware in a safe, waterproof manner; and a battery box, 21, to hold a battery or batteries and a floating charger in a secure, waterproof setting; and UV sensor cluster 13 comprising one or multiple UVA/UVB sensor(s) 13a and its rotational engine 13b comprised of a rotational motor, a motor controller board, a magnetic arm and UV sensor holder arm, used to enable a controlled rotation of the UV sensor(s).

Figure 6:
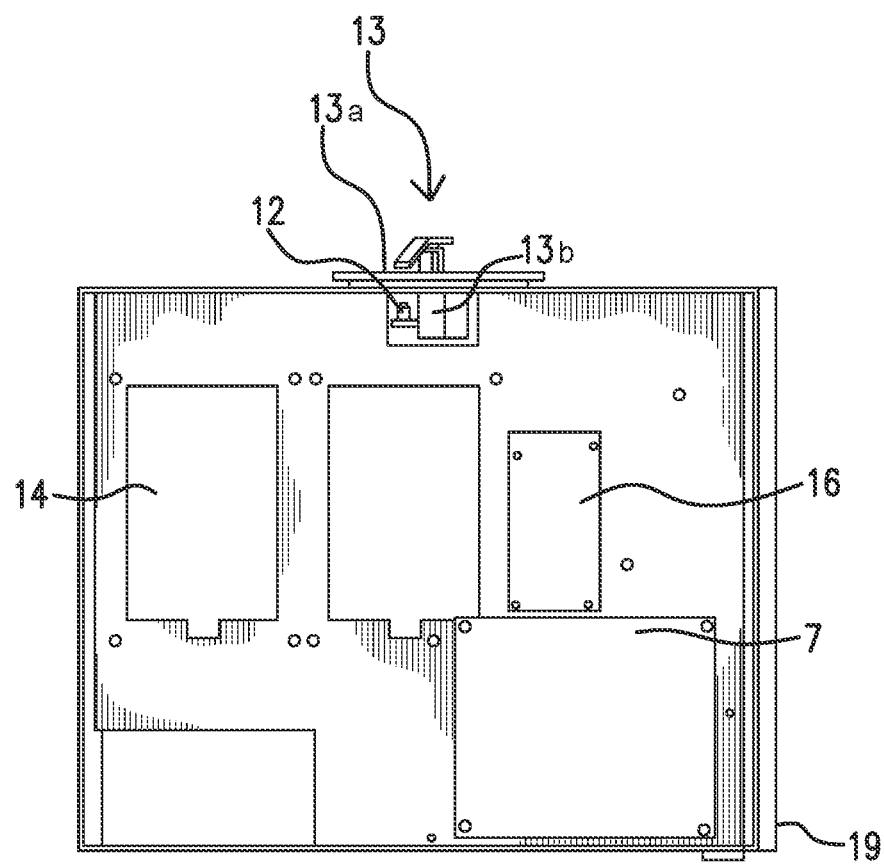
FIG. 6 is a rear view of the top portion with the cover removed of an embodiment of the device of the present invention illustrating the components inside the top portion of the device.

FIG. 6 is a rear view of the top portion with the cover removed of an embodiment of the device of the present invention illustrating the components inside the top portion/head unit of the device. Shown are a UV sensor cluster and holder, 13, known as "artificial sunflower", that reads a UV index in a rotating fashion to capture readings from all directions, mounted on a rotational motor of the rotational engine 13b; a circuit board with integrated processor, 7, for programming and running the operations of the full display unit; full assembly flip digits, 14, used to show a sun safety awareness index; a head assembly magnet sensor and board, 12, used to sense position or rotation to control the UV detector from moving further once a full rotation is reached; and colored LEDs or other digital or electromechanical structure, 16, used to show UV index on scale, with optionally increased flashing of lights based on the intensity of the UV radiation.

EXAMPLES

The following examples further describe and demonstrate embodiments within the scope of the present invention. The Examples are given solely for purpose of illustration and are not to be construed as limitations of the present invention, as many variations thereof are possible without departing from the spirit and scope of the invention.

Example 1: SOLaware™ Sun Safety Display and Dispenser Device

Figure 7:
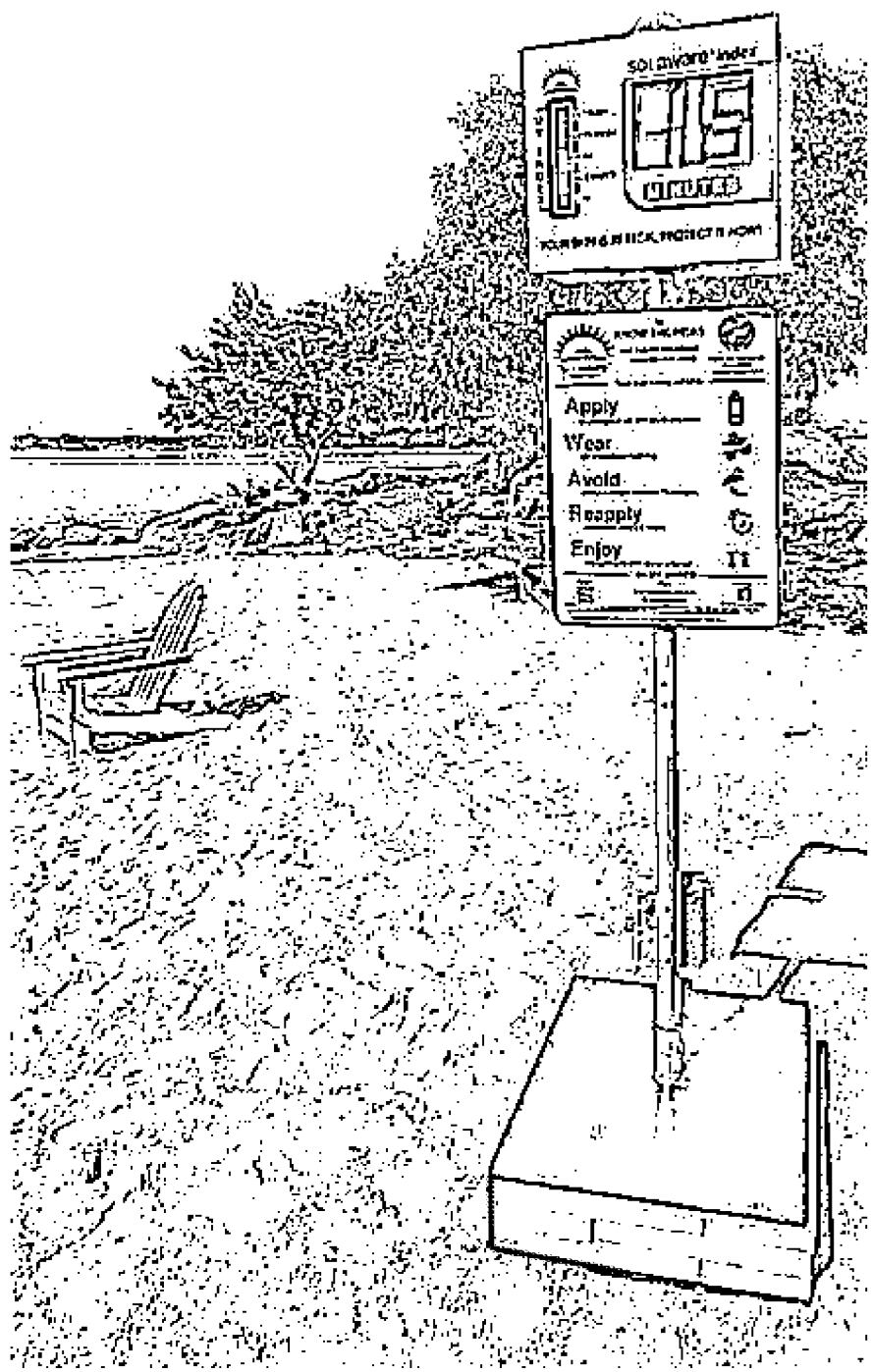
FIG. 7 shows a black and white photo of an embodiment of the device of the present invention in use at an outdoor location.

The device SOLaware™ Sun Safety Display and Dispenser device of FIG. 7 is set up by a beach on a sunny day to allow a consumer to monitor their sun exposure and to dispense a dose of a topical sunscreen product for application to the skin to provide the consumer with customized sun protection.

Figure 8:
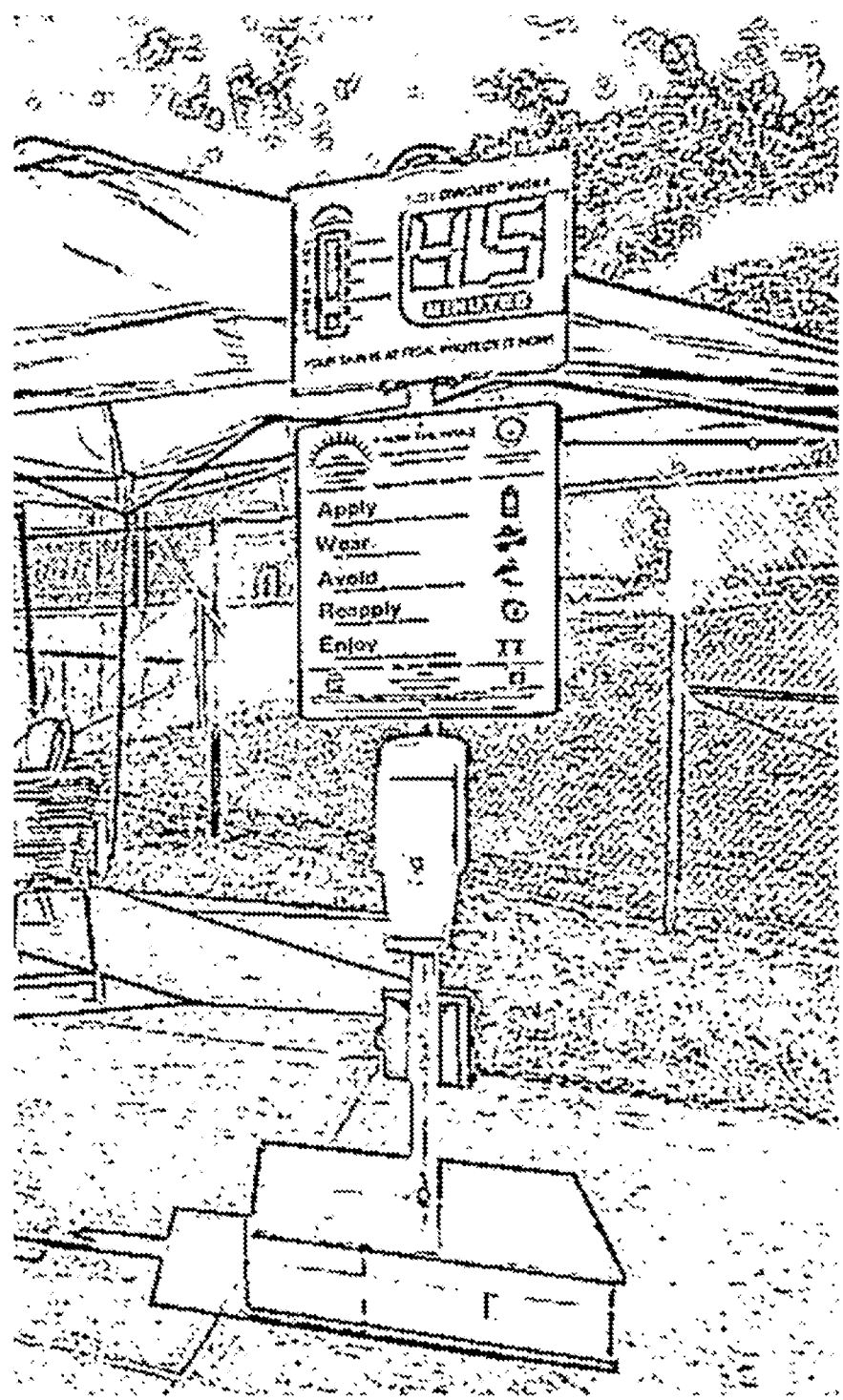
FIG. 8 shows a black and white photo of an embodiment of the device of the present invention, comprising a sunscreen dispenser, in use at an outdoor location.

The example of FIG. 8 shows that the SOLaware™ Sun Safety Display and Dispenser device is useful to warn a consumer of the time to skin burn and or potential damage; to provide a general SOLaware Index™ to help the user determine the appropriate SPF sunscreen, manually or automatically; and, to dispense sunscreen generally or by specific SPF as correlated with the user's personalized SOLaware Index™.

INCORPORATION BY REFERENCE

The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

EQUIVALENTS

The invention can be embodied in other specific forms without departing from the spirit or essential characteristics thereof. The foregoing embodiments are to be considered in all respects illustrative rather than limiting on the invention described herein. In the various embodiments of the methods and systems of the present invention, where the term comprises is used with respect to the recited steps of the methods or components of the compositions, it is also contemplated that the methods and compositions consist essentially of, or consist of, the recited steps or components. Furthermore, it should be understood that the order of steps or order for performing certain actions is immaterial so long as the invention remains operable. Moreover, two or more steps or actions can be conducted simultaneously.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

Furthermore, it should be recognized that in certain instances a composition can be described as being composed of the components prior to mixing, because upon mixing certain components can further react or be transformed into additional materials.

All percentages and ratios used herein, unless otherwise indicated, are by weight.

What is claimed is:

1. A device for monitoring and displaying solar exposure risk for human skin comprising:
   (a) two or more light sensing detectors for measuring an instantaneous solar energy density at a location in proximity to a human subject, wherein the two or more light sensing detectors are movable,
   (b) a computer system for calculation of the solar exposure risk, the computer system comprising
      (i) a computer processor,
      (ii) a computer readable storage device, and
      (iii) a computer program,
   (c) one or more display monitors,
   (d) one or more interfaces connecting the two or more light sensing detectors to the computer system,
   (e) one or more optional interfaces connecting the two or more light sensing detectors, and
   (f) an interface connecting the computer system to the one or more display monitors,
wherein the device displays an instantaneous solar exposure risk for human skin based on the instantaneous solar energy density.

2. The device according to claim 1 wherein at least one of the two or more light sensing detectors is oriented to detect and measure a direct solar energy density and wherein at least one of the two or more light sensing detectors is oriented to detect and measure reflected solar energy density.

3. The device according to claim 1 further comprising a rotational engine, including a rotational motor, a for continuously moving the two or more light sensing detectors.

4. The device according to claim 3 wherein the rotational engine for continuously moving the two or more light sensing detectors moves the two or more light sensing detectors in an oscillating motion through a partial circular path.

5. The device according to claim 1 that further comprises a sensor for measuring one or more skin characteristics of the human subject, and wherein the device calculates and displays an output parameter that further comprises an individualized solar exposure risk level for the human subject.

6. The device according to claim 5 wherein the one or more skin characteristics are selected from skin color, melanin content, melanin density, skin temperature, and moisture content.

7. The device according to claim 5 wherein the output parameter further comprises a sunscreen application recommendation for the human subject.

8. The device according to claim 7 that further comprises a dispenser for containing and dispensing a sunscreen product.

9. The device according to claim 8, wherein the dispenser dispenses the sunscreen product based on the output parameter for the human subject.

10. The device according to claim 1 wherein the two or more light sensing detectors are movable using an automated device for tracking the solar energy.

11. The device according to claim 1 wherein the display monitor displays the instantaneous solar exposure risk in digital format as a numerical value.

12. The device according to claim 1 wherein the display monitor displays the instantaneous solar exposure risk in digital format as a color coded value.

13. The device according to claim 1 further comprising a mounting pole.

14. The device according to claim 13 further comprising a base into which the mounting pole is mounted.

15. The device according to claim 14 that is stationary.

16. The device according to claim 14 that is mobile.

17. The device according to claim 1 wherein the device displays an instantaneous generalized solar exposure risk for human skin based on the instantaneous solar energy density.

18. The device according to claim 1 wherein the device displays an instantaneous personalized solar exposure risk for human skin based on the instantaneous solar energy density.

19. A method for providing a general solar exposure risk index for human skin using the device of claim 1.

20. A method for providing a personalized solar exposure risk index for human skin using the device of claim 1.

21. A method for providing a personalized solar exposure risk index for human skin and dispensing an amount and SPF level of a sunscreen product using the device of claim 1.

22. The device according to claim 1, wherein the two or more light sensing detectors measure solar energy density in $mW/cm^2$.

* * * * *